(12) United States Patent
Nelson et al.

(10) Patent No.: US 7,456,216 B2
(45) Date of Patent: Nov. 25, 2008

(54) METHODS FOR THE PREPARATION AND FORMULATION OF L-CARNITINE VALPROATE SALTS

(75) Inventors: Deanna Jean Nelson, Raleigh, NC (US); Navdeep Balkrishna Malkar, Cary, NC (US)

(73) Assignee: BioLink Life Sciences, Inc., Cary, NC (US)

( * ) Notice: Subject to any disclaimer, the term of this patent is extended or adjusted under 35 U.S.C. 154(b) by 0 days.

(21) Appl. No.: 11/725,378

(22) Filed: Mar. 19, 2007

(65) Prior Publication Data

US 2008/0234378 A1    Sep. 25, 2008

(51) Int. Cl.
*A61K 31/195* (2006.01)
*C07C 229/00* (2006.01)

(52) U.S. Cl. ...................................... 514/561; 562/567
(58) Field of Classification Search .................... None
See application file for complete search history.

(56) References Cited

FOREIGN PATENT DOCUMENTS

IT    EP 0637449 A1  *  2/1995

* cited by examiner

*Primary Examiner*—Paul A Zucker

(57) ABSTRACT

The present invention relates to methods for preparing an L-carnitine valproate salt and administering this compound to a subject in need of treatment with valproate. Pharmaceutical compositions are also provided that are useful therapies for the treatment of neurological, immunological, and viral-mediated disorders in warm-blooded mammals.

11 Claims, 3 Drawing Sheets

METHODS FOR THE PREPARATION AND FORMULATION OF L-CARNITINE VALPROATE SALTS

FIELD OF THE INVENTION

The present invention relates to methods for preparing L-carnitine valproate salts of alkaline earth metals and administering these compounds, either independently or in combination with another drug or L-carnitine valproate salt, to a subject in need of treatment with valproate. Pharmaceutical compositions are also provided that are useful therapies for the treatment of neurological, immunological, and retroviral-mediated disorders in warm-blooded mammals.

BACKGROUND OF THE INVENTION

Valproic acid (Chemical Abstracts Service (CAS) Registry No. 99-66-1) is a branched carboxylic acid having the molecular formula $C_8H_{16}O_2$. Valproic acid is also known as 2-propylpentanoic acid, 2-propylvaleric acid, and dipropylacetic acid. Valproic acid is a colorless liquid having a boiling point of 120-121° C. at 14 torr. The compound is very slightly soluble in water. It has a pKa of 4.6, and reacts with bases to form salts generally known as valproates.

Clinical Uses

Since its introduction into the clinical practice in the 1970's, valproic acid (valproate) has been approved by regulatory agencies around the world, including the U.S. Food and Drug Administration (FDA), as a therapy for several clinical indications, including neurological disorders, mania, manic episodes associated with bipolar disorder, convulsions, epilepsy, and affective and attention deficit disorders. In addition, valproate is used for the prophylactic treatment, modulation and management of migraine headache, chronic pain, and neuropathic pain.

Further, potential therapeutic benefits of valproate in still other clinical indications are being evaluated in on-going clinical trials. Valproate therapy is being evaluated in clinical studies assessing activity of the substance as a histone deacetylase inhibitor to promote cell differentiation and regeneration, or to regulate gene expression in subjects afflicted with spinal muscular atrophy. Likewise, valproate may exhibit therapeutic benefit as a combinatorial therapeutic treatment of human cancers and for the treatment of tumor metastasis. Similarly, valproate may be useful in the treatment and management of pain, for treating severe tinnitus, for treatment of disorders of personal attachment and deficient social interaction, or for treating Alzheimer's disease. Preclinical studies also show that valproate may promote neural stem cell differentiation and or be useful as a co-medicament to promote the elimination of the Human Immunodeficiency Virus (HIV) or other retroviruses from the body or to prevent progression of a retroviral infection to AIDS.

Although the underlying therapeutic mechanisms are unclear, a growing body of evidence suggests that valproate has neuroprotective and neurotrophic actions. For example, both brain imaging and post-mortem studies demonstrate that bipolar disorder involves a decrease in the volume and number of neurons and glia in discrete brain areas thought to be important for cognition and mood regulation. Remarkably, the reduction in brain volume in bipolar patients was found to be largely suppressed by chronic treatment with valproate, in part as a consequence of its histone deacetylase inhibition. [Kanai H, Saws A, Chen R W, Leeds P, Chuang D M. Valproic acid inhibits histone deacetylase activity and suppresses excitotoxicity-induced GAPDH nuclear accumulation and apoptotic death in neurons. Pharmacogenom J 2004; 4: 336-344.] Likewise, in cellular models, valproate protects rat cerebral cortical neurons and cerebellar granule cells from glutamate-induced excitotoxicity and apoptotic death from stress on the endoplasmic reticulum in C6 glioma cells and PC12 cells. [Bown C D, Wang J F, Chen B, Young L T. Regulation of ER stress proteins by valproate: therapeutic implications. Bipolar Disord 2002; 4: 145-151.] In a rat model of stroke, post-insult valproate treatment reduces ischemia-induced brain damage, caspase-3 activation and neurological deficits. [Ren M, Leng Y, Jeong M, Leeds P R, Chuang D M. Valproic acid reduces brain damage induced by transient focal cerebral ischemia in rats: potential roles of histone deacetylase inhibition and heat shock protein induction. J Neurochem 2004; 89: 1358-1367.] A number of studies report that valproate activates cell survival factors such as Akt, extracellular signal-regulated protein kinase, and cyclic AMP response element binding protein. [De Sarno P, Li X, Jope R S. Regulation of Akt and glycogen synthase kinase-3 beta phosphorylation by sodium valproate and lithium. Neuropharmacology 2002; 43: 1158-1164. Yuan P X, Huang L D, Jiang Y M, Gutkind J S, Manji H K, Chen G. The mood stabilizer valproic acid activates mitogen-activated protein kinases and promotes neurite growth. J Biol Chem 2001; 276: 31674-31683. Einat H, Yuan P, Gould T D, Li J, Du J, Zhang L, et al. The role of the extracellular signal-regulated kinase signaling pathway in mood modulation. J Neurosci 2003; 23: 7311-7316.] Additionally, valproate induces cytoprotective proteins such as Bcl-2, Grp78, brain-derived neurotrophic factor, and heat-shock protein 70. [Chen G, Zeng W Z, Yuan P X, Huang L D, Jiang Y M, Zhao Z H et al. The mood-stabilizing agents lithium and valproate robustly increase the levels of the neuroprotective protein bcl-2 in the CNS. J Neurochem 1999; 72: 879-882.] Moreover, valproate promotes neurite outgrowth. [Yuan P X, Huang L D, Jiang Y M, Gutkind J S, Manji H K, Chen G. The mood stabilizer valproic acid activates mitogen-activated protein kinases and promotes neurite growth. J Biol Chem 2001; 276: 31674-31683.] Recently, valproate was shown to protect dopaminergic neurons in midbrain neuron/glia cultures by stimulating the release of neurotrophic factors from astrocytes. [Chen P-S, Peng G-S, Li G, Yang S, Wu X, Wang C-C, Wilson B, Lu R-B, Gean P-W, Chuang D-M, Hong J-S. Valproate protects dopaminergic neurons in midbrain neuron/glia cultures by stimulating the release of neurotrophic factors from astrocytes. Molec Psych 2006; 11: 1116-1125.] Further, valproate at therapeutic levels was reported to inhibit histone deacetylase (HDAC), an enzyme that catalyzes the remove of acetyl groups from lysine residues of histones, thereby altering gene expression. [Phiel C J, Zhang F, Huang E Y, Guenther M G, Lazar M A, Klein P S. Histone deacetylase is a direct target of valproic acid, a potent anticonvulsant, mood stabilizer, and teratogen. J Biol Chem 2001; 276: 36734-36741. Gottlicher M, Minucci S, Zhu P, Kramer O H, Schimpf A, Giavara S et al. Valproic acid defines a novel class of HDAC inhibitors inducing differentiation of transformed cells. EMBO J. 2001; 20: 6969-6978.]

Sources of the Active Pharmaceutical Ingredient Valproate

Although valproate is a therapeutically active pharmaceutical ingredient, valproic acid is an oil that is difficult to formulate and use in the preparation of dosage forms suitable for human or veterinary use. Pharmaceutical and pharmacological advantages are gained when therapeutic dosage forms are prepared from alkali metal or alkaline earth metal salts of valproic acid. Therefore, alkali metal or alkaline earth metal salts of valproic acid are used in present-day clinical formulations as sources of the active drug ingredient, valproate.

Sodium ($Na^{1+}$), calcium ($Ca^{2+}$) and magnesium ($Mg^{2+}$) valproates have been evaluated for use in pharmaceutical and veterinary compositions. Sodium valproate is a hygroscopic salt that is difficult to formulate into pharmaceutical formulations. In contrast, non-stoichiometric valproate sodium compounds comprising combinations of sodium valproate and valproic acid (divalproex sodium, for example) are not hygroscopic, and are bioavailable and therapeutically active sources of valproate. (The non-stoichiometric compound known as divalproex sodium is disclosed in U.S. Pat. No. 4,988,731, for example, and one of its therapeutic embodiments is described in the FDA Approved Labeling Text for NDA 21-168, Aug. 4, 2000.) At the present time, divalproex sodium is the most commonly formulated source of the drug valproate.

Calcium valproate has also been evaluated for use in pharmaceutical and veterinary formulations. Methods for the preparation of calcium salts of valproic acid are disclosed in U.S. Pat. No. 4,895,873. Although pharmaceutical formulations comprising calcium valproate have been approved by the regulatory bodies of several countries, the use of this valproate salt has been severely restricted following publication of reports of adverse toxicological and reproductive effects in dogs, rats, mice, rabbits, and rats. (For example, adverse effects caused by calcium valproate administration are reported in "Calcium valproate-induced uterine adenocarcinomas in Wistar rats" by Watkins, Gough, et al. in Toxicology, Vol. 41, pages 35-47, 1993.)

Magnesium valproate is also used in clinical formulations. Magnesium valproate, which has the CAS Registry No. 62859-43-7, a molecular formula of $C_{16}H_{30}O_4Mg$, and a molecular weight of 310.71, is also known as magnesium 2-propylvalerate and as 2-propylpentanoic acid magnesium salt. By weight, its composition is 61.8% carbon, 9.7% hydrogen, 7.8% magnesium, and 20.6% oxygen.

Clinical investigators have reported that magnesium valproate possesses pharmacokinetic properties comparable to sodium valproate or valproic acid, is hydrolyzed to valproic acid and magnesium ions upon absorption in the bloodstream, and has important advantages in comparison with either sodium valproate or valproic acid. Among the therapeutic advantages of magnesium valproate are the clinical observations that magnesium valproate exhibits a slower and more regular absorption rate, which prevents the variations in plasma levels of valproate typically observed when sodium salts of valproic acid are administered. Additional therapeutic benefits are afforded by magnesium ions, which possess anticonvulsant and sedative properties. [X. Rabasseda, Drugs of Today, Vol. 31, No. 3, 1995, pp. 185-190.] In contrast to calcium valproate, which exacerbates malignancy, magnesium valproate is a useful therapy when administered to patients with cervical cancer. For example, Chavez-Blanco et al. have reported that magnesium valproate at a dose between 20 and 40 mg/kg inhibits deacetylase activity and hyperacetylates histones in tumor tissues. [A. Chavez-Blanco, B. Segura-Pacheco, et al., Molecular Cancer Jul. 7, 2005, Vol. 4, pp. 22ff.]

Spanish Patent No. ES 430062 discloses one method for the preparation of magnesium valproate in which valproic acid is allowed to react with magnesium oxide in alcoholic medium. The method has the following shortcomings. The reaction is carried out in a suspension. Reaction times are lengthy. The final product is contaminated with unreacted magnesium oxide, which comingles with the desired product when acetone is added to precipitate the magnesium valproate. The resulting product is an amorphous solid that is difficult to purify and dry. The product has poor bioavailability.

In U.S. Pat. No. 5,180,850 to Cavazza, a method is disclosed for the preparation of crystalline magnesium valproate. (The same procedure is disclosed in Italian Patent No. 2,283,789 and in EP 433,848 B1.) According to the method of Cavazza, valproic acid is reacted with a substantially stoichiometric amount of a magnesium alkoxide selected from magnesium ethoxide, magnesium propoxide, and magnesium isopropoxide in methanol or ethanol. The magnesium salt of valproic acid is isolated in a microcrystalline form by solvent evaporation or by acetone precipitation. The method has the following shortcomings. Product isolation by solvent evaporation provides product that is contaminated by incompletely reacted starting materials or adventitious contaminants in starting materials or solvents. When the reaction is carried out in ethanol, the quantity of magnesium ethoxide specified is not completely dissolved in the volume of ethanol taught. Although some conversion to magnesium valproate occurs, the method does not permit control of temperature, reaction time, removal of impurities, etc. When the reaction is carried out in methanol, the addition of acetone fails to precipitate the product, using the volume of acetone taught in the patent.

In U.S. Pat. No. 6,753,349, Weh discloses a method for producing compositions containing at least one molecule of a valproic acid salt and at least one molecule of valproic acid. The valproic acid salt represents an alkali or alkaline earth salt of valproic acid, wherein the alkali salt is a valproate salt of lithium, sodium, potassium, or rubidium, and the alkaline earth salt of valproic acid is a valproate salt of magnesium, calcium, strontium, or barium. Preferably, the valproate salt is a sodium, potassium, magnesium or calcium salt. The compounds of Weh's invention have the general formula:

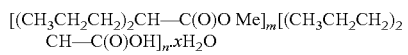

in which Me is $Li^{1+}$, $Na^{1+}$, $K^{1+}$, $Rb^{1+}$, $Mg^{2+}$, $Ca^{2+}$, $Sr^{2+}$, or $Ba^{2+}$, preferably $Na^{1+}$, $K^{1+}$, $Mg^{2+}$, or $Ca^{2+}$; m is an integer from 1 to 10, preferably from 1 to 6, n is an integer from 1 to 9, preferably from 1 to 3, and the ratio m:n is from 1:1 to 6:1, preferably 1:1 to 5:3 and particularly preferably 1:1, 4:3, or 2:1; and x is zero, 1 or 2, preferably zero or 1. In general, the method of preparing magnesium valproate compositions of Weh's invention comprises combining a selected amount of magnesium carbonate, magnesium bicarbonate, or combinations thereof with a selected amount of valproic acid to form a reaction mixture; and allowing the valproic acid to react directly with the magnesium carbonate, magnesium bicarbonate, or combinations thereof under conditions where the reaction temperature is controlled above the melting point of valproic acid. The methods exhibit the following shortcomings. Neither U.S. Pat. No. 6,753,349 nor related international patents WO 2001/032595 and EP 1,230,205 B1 disclose methods for the preparation of each of the several magnesium valproate compositions that are disclosed in these patents. In the absence of data disclosing the ratios of magnesium carbonate and/or magnesium bicarbonate that must be employed to obtain one of the several magnesium valproate compositions that are disclosed by Weh, a knowledgeable artisan must undertake extensive experiments in order to define a process suitable for pharmaceutical manufacturing. Further, valproic acid is an oil and not a solid with a known melting point, so omission in the disclosure of an optimal reaction temperature also requires extensive experimentation. The final product is contaminated with unreacted magnesium carbonate or bicarbonate, as well as other magnesium valproate salts, all of which comingle with the desired product. No methods for product purification are disclosed. The bioavailability of Weh's magnesium valproate compositions is not reported.

After receiving valproate in its conventional compositions, patients frequently experience deleterious side effects, including gastrointestinal distress and ulceration and occasionally, life-threatening hepatic dysfunction. Hepatotoxicity induced by valproate is characterized by microvesicular periportal steatosis and distorted mitochondria. [H Zimmerman, K Ishak. Valproate-induced hepatic injury: analyses of 23 fatal cases. Hepatology 1982; 2: 591-597.] Studies in animal models and human subjects indicate that following valproate administration, the hepatic levels of free Coenzyme A (CoA) are decreased, and the hepatic levels of medium chain acyl CoA compounds are increased. The co-administration of L-carnitine blocks the development of valproate-induced steatosis. [T P Bohan, P Rogers, C R Roe. Valproate and carnitine. In: *Current Concepts in Carnitine Research* (A L Carter, Ed.), CRC Press, Boca Raton, Fla., 2000, pp. 19-26.]

L-(−)-Carnitine is a vitamin-like nutrient that is essential for energy production and fat metabolism in the physiological systems of birds, fish, and mammals. The structure of L-carnitine is:

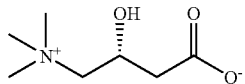

L-carnitine is supplied to the body through both endogenous synthesis (about 25% of the adult daily requirement) and food intake (about 75% of the adult daily requirement). The main dietary source of L-carnitine is meat; beef and lamb provide the most dietary L-carnitine. (Fruits and vegetables provide only traces of L-carnitine.) Within the human body, the major sites of L-carnitine biosynthesis are the liver and kidney, as well as the brain and testes. Biosynthesis requires lysine, methionine, vitamin C, iron, vitamin $B_6$, and niacin. L-carnitine is an essential nutrient for infants, since neonates and young children lack the capacity to synthesize L-carnitine in the quantities that are needed for optimal development.

L-(−)-Carnitine functions as a requisite mediator of acyl transport and accepts acyl groups from a variety of acylCoA derivatives in cells and tissues throughout the body. In humans, the transport activity of L-carnitine is particularly important in working muscle, for example, in the skeletal muscles and the heart. Both types of tissues are dependent on fatty acid metabolism for energy supply, and L-carnitine mediates the translocation of fatty acyl groups across mitochondrial membranes to the sites of oxidation in the mitochondria. In addition, L-carnitine shuttles short chain fatty acids from inside the mitochondria to the cytosol. Other physiological roles of L-carnitine include mitochondrial long-chain fatty acid oxidation, buffering of the mitochondrial acyl CoA/CoA couple, scavenging acyl groups, peroxysomal fatty acid oxidation, branched-chain amino acid oxidation, and membrane stabilization.

Because L-carnitine functions as a requisite mediator of acyl transport in the body, an L-carnitine deficiency is a serious physiological disorder. Individuals who suffer from L-carnitine deficiency are afflicted with muscle weakness (myasthenia), accompanied by an accumulation of lipids in specific types of muscle fibers. Severe L-carnitine deficiency may present as myasthenia gravis. Individuals who suffer from systemic L-carnitine deficiency and also secondary L-carnitine deficiency associated with organic acidemias may experience vomiting, stupor, confusion and in severe or prolonged occasions of systemic L-carnitine deficiency accompanied by stressful stimuli, coma in encephalopathic episodes.

Given the facts that valproate induces liver steatosis and L-carnitine deficiency, that L-carnitine is a requisite mediator of acyl transport in the body, and that neonates and young children lack the ability to synthesize L-carnitine (vide infra), it is not surprising that young age and polytherapy including valproate are the primary risk factors for valproate-induced L-carnitine deficiency and valproate-related hepatic failure. [T P Bohan, P Rogers, C R Roe. Valproate and carnitine. In: *Current Concepts in Carnitine Research* (A L Carter, Ed.), CRC Press, Boca Raton, Fla., 2000, pp. 19-26.] An incomplete diet, physiological stress situations, such as exercise or pregnancy, and metabolic dysfunction, in particular, lipid disorders or diseases of the liver and kidney, also induce L-carnitine deficiency and create a need for L-carnitine supplementation in adults; this need is increased when valproate is administered.

There are, however, known difficulties in formulating L-carnitine. For example, it is known that L-carnitine is hygroscopic. The hygroscopicity of L-carnitine causes a lack of storability of the solid substance and of simple powder mixtures prepared therefrom, and causes problems such as inadequate flowability during further formulating, processing, and manufacturing of orally administrable dosage forms of pure solid L-carnitine or powdered mixtures containing L-carnitine for use in food, nutritional or dietary supplements for humans or other mammals, animal feed or dietary supplements, or drugs for human or veterinary use. However, oral dosage forms represent the preferred dosage forms, inasmuch as they make it particularly easy for users to take the active ingredient and comply with optimal dosage regimens.

Further, it is known that L-carnitine exhibits a distinctly repugnant malodor and a distinctly objectionable taste after ingestion. The noxious odor and taste render ingestion of oral dosage forms of L-carnitine difficult and interfere with compliance to optimal dosage regimens. Thus, there is a significant unmet need for a form of L-carnitine that is free from noxious odor or taste that can be administered to address L-carnitine deficiency.

Patients receiving conventional valproate compositions often must conform to complex dosing regimens. In addition to valproate, individuals may be taking other medications. Therefore, the addition of a dosage of supplemental L-carnitine often adds a new level of complexity to an already complicated dosing regimen for these patients.

Further, although there are numerous case reports and case series in the literature documenting valproate-induced L-carnitine deficiency, there are very few reports of the carnitine levels in the general patient population. L-Carnitine is not routinely monitored in patients receiving valproate, and unrecognized L-carnitine deficiency may develop unexpectedly in these subjects.

A consideration of all of the facts presented heretofore indicates clearly that there is a significant unmet need for a composition that concomitantly provides therapeutic quantities of both valproate and L-carnitine. The present invention remedies this need.

GENERAL DESCRIPTION OF THE INVENTION

Valproate is a drug commonly used to treat seizures, bipolar disorder, and migraine headaches. Clinically relevant L-carnitine deficiency related to valproate administration is well established in patient populations susceptible to carnitine deficiency, i.e., neonates, children, and adults experiencing stress. The present invention provides an L-carnitine valproate composition having the molecular formula $C_{23}H_{45}NO_7M^{2+}$, wherein $M^{2+}$ is calcium or magnesium. The L-carnitine valproate composition comprises L-carnitine, calcium or magnesium, and valproate in a stoichiometric ratio of 1:1:2. The invention further provides a method for preparing an L-carnitine valproate composition, comprising combining a calcium or magnesium compound, L-carnitine, and valproic acid in a stoichiometric ratio of 1:1:2 in water or an aqueous alcohol solution, and isolating the L-carnitine valproate composition. In addition, the invention provides a pharmaceutical formulation for the concomitant administration of L-carnitine and valproate, comprising an L-carnitine alkaline earth metal valproate, wherein the alkaline earth metal is calcium or magnesium. Methods of the present invention provide formulations comprising a dosage form comprising a quantity of an L-carnitine valproate salt of an alkaline earth metal that is sufficient to provide a therapeutically effective first amount of valproate and a therapeutically effective second amount of L-carnitine to a warm-blooded animal. Further, the dosage form is a solid or a liquid dosage form.

DETAILED DESCRIPTION OF THE INVENTION

Figure 1:
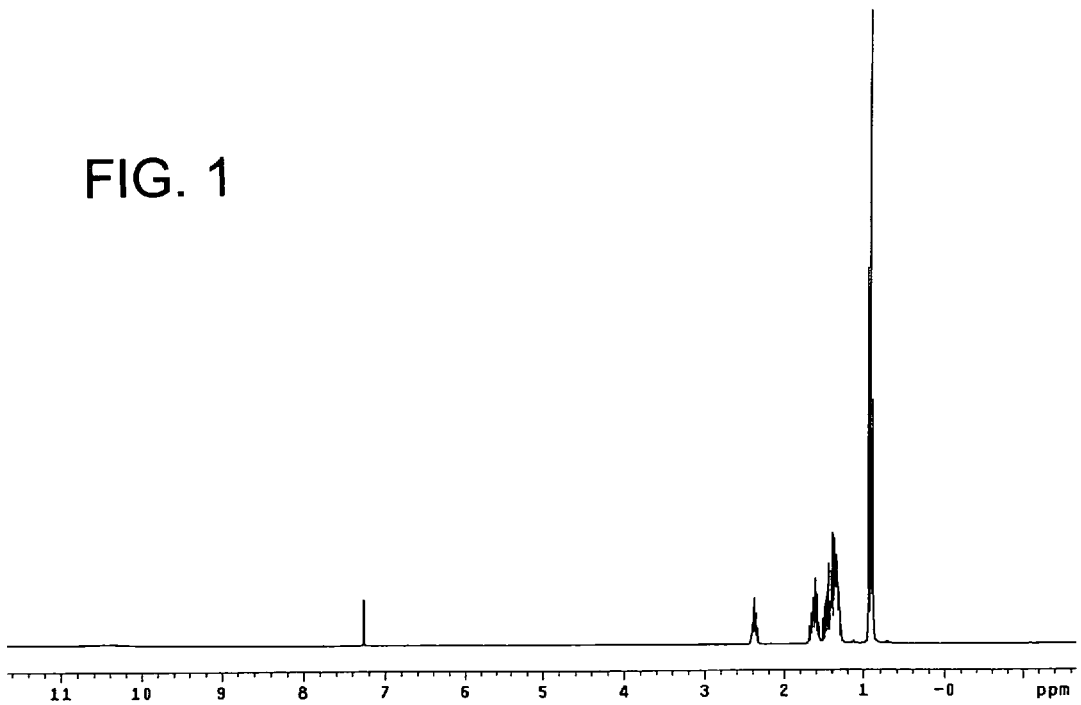
FIG. 1 is the $^1$H-Nuclear Magnetic Resonance ($^1$H-NMR) spectrum of valproic acid in perdeutero-methanol solution.

The present invention relates to methods for preparing L-carnitine valproate salts of alkaline earth metals, wherein the alkaline earth metal is calcium or magnesium. Both L-carnitine calcium valproate and L-carnitine magnesium valproate, two embodiments of the present invention, are bioavailable sources of valproate, a drug that is useful for several clinical indications, including neurological disorders, including mania, manic episodes associated with bipolar disorder, epilepsy, and affective and attention deficit disorders. In addition, valproate is used for the prophylactic treatment, modulation and management of migraine headache, chronic pain, and neuropathic pain. The L-carnitine valproate salts of the present invention concomitantly provide L-carnitine, a compound that is known to be deficient in subjects receiving valproate.

The present invention also relates to a method of formulating L-carnitine valproate salts of alkaline earth metals in solid dosage forms or in water or aqueous solutions in concentrations that provide a therapeutically effective first amount of valproate and a therapeutically effective second amount of L-carnitine to a warm-blooded animal after the formulation is administered to the animal.

The present invention provides L-carnitine valproate salts of alkaline earth metals which are heretofore unknown valproate salts. CAS Registry Numbers have not yet been assigned to these substances. The molecular formula of an L-carnitine valproate salt of the present invention is $C_{23}H_{45}NO_7M^{2+}$, wherein $M^{2+}$ is calcium or magnesium. The L-carnitine valproate salts of the present invention are true salts, not merely admixtures of L-carnitine and valproate.

Among the physico-chemical properties that are exhibited by these L-carnitine valproate salts are unique melting points, and solubility in water and aqueous solutions. The L-carnitine valproate salts of the present invention have no objectionable taste.

Also within the scope of this invention are L-carnitine valproate salt compositions having specific bulk densities or tap densities, and L-carnitine valproate salt compositions having specific particle sizes. Further included within the scope of this invention are L-carnitine valproate salt compositions coated with pharmaceutically acceptable materials intended to modify the release and/or bioavailability of the L-carnitine valproate salt of the present invention (e.g., Eudragit, microcrystalline cellulose, hydroxypropylmethylcellulose phthalate, and so forth).

According to the methods of the present invention, an L-carnitine valproate salt of an alkaline earth metal is administered, alone or in combination with other therapeutically active or inactive substances, as a therapeutically effective and biologically available (i.e., bioavailable) source of L-carnitine and valproate that is concomitantly useful for the treatment of neurological, immunological, and viral-related disorders and for the prevention and/or treatment of L-carnitine deficiency.

The term "excipient material" means any compound forming a part of the formulation, which is not intended to have independent biological activity, and which is added to a formulation to provide specific characteristics to the dosage form, including providing protection to the active ingredient from chemical degradation, facilitating release of a tablet or caplet from the contact surfaces of manufacturing equipment, and so forth.

The term "true salt" as used herein generally means a salt comprising a metal cation and associated anions, each present in sufficient number to provide charge balance. A true salt has a composition, a molecular weight, and other physico-chemical properties such as melting point that are characteristic of the salt.

By the terms "treating" and "treatment" and the like are used herein to generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein encompasses any treatment of a disease in a mammal, particularly a human and includes: (a) preventing the disease from occurring in a subject which may be predisposed to the disease but has not yet been diagnosed as having it; (b) inhibiting the disease or arresting its development; or (c) relieving the disease, causing regression of the disease and/or its symptoms or conditions.

The phrase "therapeutically effective" is intended to qualify the amount of an L-carnitine valproate salt for use in the orally or intravenously administered therapy which will achieve the goal of providing a biologically available (i.e., bioavailable) concentration of the drug valproate to effect reducing or preventing, for example, a neurological, immunological, or viral-related disorder, while avoiding adverse side effects typically associated with valproic acid, sodium valproate compositions, or other valproate salts.

Included within the scope of this invention is a method of treating neurological disorders, immune disorders, or viral-related disorders in a warm-blooded animal using pharmaceutical compositions comprising L-carnitine valproate salts of the present invention and a suitable pharmaceutical carrier.

For the purpose of this disclosure, a warm-blooded animal is a member of the animal kingdom which includes but is not limited to mammals and birds. The most preferred mammal of this invention is human.

Surprisingly, the inventors have discovered heretofore unknown valproate salts, L-carnitine valproate salts of alkaline earth metals. Each L-carnitine valproate salt of the present invention is a white solid having the molecular formula $C_{23}H_{45}NO_7M^{2+}$, wherein $M^{2+}$ is calcium or magnesium. Each L-carnitine valproate salt of the present invention has the molecular structure:

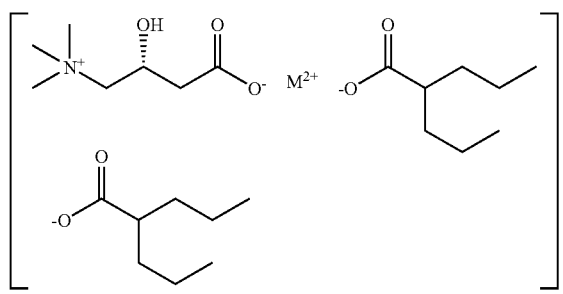

wherein $M^{2+}$ is calcium or magnesium. The L-carnitine valproate salts of the present invention are true salts, not admixtures of L-carnitine, an alkaline earth metal ion, and valproate. Among the physico-chemical properties that each salt exhibits are a characteristic melting point, and solubility in water and aqueous solutions. An L-carnitine calcium valproate salt of the present invention has no odor and no objectionable taste. An L-carnitine magnesium valproate salt of the present invention has a slight odor and no objectionable taste.

L-Carnitine calcium valproate of the present invention is a white solid having the molecular formula $C_{23}H_{45}NO_7Ca$ and a molecular weight of 487.77 grams per mole. The molar ratio of L-carnitine to calcium to valproate in L-carnitine calcium valproate is 1:1:2. By weight, its composition is 56.6% carbon, 9.3% hydrogen, 8.2% calcium, 2.9% nitrogen, and 23.0% oxygen. L-Carnitine calcium valproate is about 58.7% valproate by weight, about 33.1% L-carnitine by weight, and about 8.2% calcium by weight. L-Carnitine calcium valproate has a melting point of about 171.2° C. (with decomposition and release of trimethylamine).

If L-carnitine calcium valproate is exposed to water vapor in the atmosphere for several days, it absorbs water from the air and is converted to a heretofore unknown hydrate. L-Carnitine calcium valproate hydrate of the present invention is a mobile, white solid having a melting point of about 112° C. (with decomposition).

L-Carnitine magnesium valproate of the present invention is a white solid having the molecular formula $C_{23}H_{45}NO_7Mg$ and a molecular weight of 472 grams per mole. The molar ratio of L-carnitine to magnesium to valproate in L-carnitine magnesium valproate is 1:1:2. By weight, its composition is 58.5% carbon, 9.6% hydrogen, 5.2% magnesium, 3.0% nitrogen, and 23.7% oxygen. L-Carnitine magnesium valproate is about 60.6% valproate by weight, about 34.2% L-carnitine by weight, and about 5.2% magnesium by weight. L-Carnitine magnesium valproate has a melting point of about 77.2° C. (with decomposition and release of trimethylamine).

When exposed to water vapor in the atmosphere for several days, L-carnitine magnesium valproate absorbs water from the air and is converted to a heretofore unknown hydrate. L-Carnitine magnesium valproate hydrate of the present invention is a nearly colorless crystalline solid having a crystalline structure of nearly transparent spars and a melting point of about 47° C. (with decomposition).

L-Carnitine calcium valproate salts of the present invention are stable when stored in a closed and sealed container. During storage under these conditions, no odor is detected. L-Carnitine magnesium salts of the present invention are stable when stored in a closed and sealed container. During storage under these conditions, a slight odor of trimethylamine is detected. Both L-carnitine calcium valproate and L-carnitine magnesium valproate are converted to the corresponding hydrates by exposure to water vapor in the atmosphere. Each hydrate has a characteristic melting point.

While not wishing to be bound by any particular hypothesis or theory, the inventors concluded from the experimental observations of lack of odor or a slight odor that an L-carnitine calcium valproate salt of the present invention is more stable than an L-carnitine magnesium valproate salt of the invention.

Surprisingly, the inventors have discovered methods for the preparation of L-carnitine valproate salts of alkaline earth metals that afford significant advantages, particularly in pharmaceutical manufacturing and formulation. For example, L-carnitine calcium valproate of the present invention, a white solid, is recovered in greater than about 85% yields from aqueous alcohol solutions containing valproic acid, L-carnitine, and calcium ion ($Ca^{2+}$), each of which is added to the reaction in no particular order. Likewise, L-carnitine magnesium valproate of the present invention, a white solid, is recovered in greater than about 85% yield from aqueous alcohol solutions containing valproic acid, L-carnitine, and magnesium ion ($Mg^{2+}$), each of which is added to the reaction in no particular order. Each L-carnitine valproate salt thus obtained has a purity of greater than about 95%, is free of contaminating inorganic and organic salts and residual solvents, and is stable during storage in closed and sealed containers. Further, an L-carnitine valproate salt of the present invention readily dissolves in water or aqueous solutions to provide aqueous solutions having a valproate concentration in the range from about 10 mg/mL to about 150 mg/mL and near neutral pH.

The process for the production of an L-carnitine valproate salt of the present invention can be performed according to the invention from a calcium or magnesium compound, L-carnitine, and valproic acid in a stoichiometric ratio of 1:1:2, respectively, in a suitable solvent, such as water, methanol, ethanol, or a mixture thereof. Calcium hydroxide, calcium oxide, calcium carbonate, and calcium chloride can be used as the calcium compound. Magnesium hydroxide, magnesium oxide, magnesium carbonate, and magnesium chloride can be used as the magnesium compound. Preferably the reaction is performed in an aqueous medium. The reaction temperature is suitably 20° C. to less than the boiling point of the solvent selected, preferably about 20° C.

According to a preferred variation of the process according to the present invention, an L-carnitine valproate salt of the present invention can be recovered from a solution of calcium or magnesium ion, valproate, and L-carnitine by concentration and precipitation. Thus, L-carnitine calcium valproate or L-carnitine magnesium valproate is recovered from the solution if the solvent, after a reaction time of several hours, is then removed by spray-drying, vacuum-drying, freeze-drying, or concentrating by evaporation, or the salt is precipitated by addition of an organic solvent. Preferably, the solution is concentrated by evaporation at reduced atmospheric pressure or by spray drying under conditions where the temperature is maintained at about 70° C. or lower to prevent degradation and evolution of trimethylamine. By spray drying, the desired product is obtained in the desired grain size. Instead of spray drying, the solution can be concentrated by evaporation at reduced atmospheric pressure (for example, by evaporation at reduced pressure on a rotary evaporator), and the resultant solid residue further treated by a purification treatment/scheme in a suitable solvent.

The inventors have discovered that simple admixture or combination of L-carnitine, a calcium or magnesium salt, and valproic acid without a suitable solvent is not sufficient to provide an L-carnitine valproate salt of the present invention. After simple admixture or combination without a suitable solvent, L-carnitine retains its objectionable malodor and offensive taste, as well as its hygroscopicity, and valproic acid remains an oil. In contrast, use of the methods of preparing the L-carnitine valproate salt of the present invention as disclosed herein provides a composition of the present invention that is free from objectionable taste and free or nearly free from repugnant odor. Further, an L-carnitine valproate salt of the present invention has different physico-chemical properties from the starting materials. As we discovered and disclose in Example 1, for example, L-carnitine calcium valproate, an embodiment of the present invention, has a melting point of 171.2° C., different from the melting point of L-carnitine (186-190° C.) or valproic acid (an oil at room temperature and above). The $^1$H-NMR spectrum of L-carnitine calcium valproate (FIG. 2) differs from that of the starting materials (i.e., L-carnitine and valproic acid) and confirms the structure. L-carnitine calcium valproate is soluble in water, and aqueous solutions of this salt provide bioavailable L-carnitine, calcium, and valproate.

As we discovered and disclose in Example 2, L-carnitine magnesium valproate, another embodiment of the present invention, is a white solid having a melting point of 77.2° C., different from the melting point of L-carnitine. The $^1$H-NMR spectrum of L-carnitine magnesium valproate (FIG. 3) differs from that of the starting materials (i.e., L-carnitine and valproic acid) and confirms the structure. L-carnitine magnesium valproate is nearly odorless and free from objectionable taste. L-Carnitine magnesium valproate is soluble in water, and aqueous solutions of this salt provide bioavailable L-carnitine, magnesium, and valproate.

The methods for the preparation of L-carnitine valproate salts that are disclosed herein are advantageously useful in pharmaceutical manufacturing of these valproate salts, as illustrated by way of example, by the following. The raw materials and solvents are commercially available. The reaction conditions enable control of reaction temperature, monitoring of the progress of reaction for extent of completion, in-process testing of the concentration of L-carnitine alkaline earth metal valproate that is present in solution and its quality and purity, methods for the removal of impurities, and convenient and high yield steps for the recovery of the L-carnitine alkaline earth metal valproate from the solution.

An L-carnitine valproate salt obtained by the methods of the present invention exhibits both the high purity and absence of both solvents and chemical and biological contaminants, qualities qualifying it for use in pharmaceutical formulations. Further, an L-carnitine valproate salt of the invention is easily milled or processed into formulary dosage forms using conventional methods and techniques.

In general, the solubilities of calcium or magnesium salts of organic acids in water or aqueous solutions vary unpredictably. Surprisingly, the inventors have found that formulations of an L-carnitine valproate salt of the present invention in aqueous solution are readily prepared by dissolving L-carnitine calcium valproate or L-carnitine magnesium valproate in water or aqueous solutions of an alcohol or polyol. In this manner, clear and colorless aqueous solutions of L-carnitine calcium valproate or L-carnitine magnesium valproate, respectively, are reproducibly obtained at valproate concentrations as great as about 300 mg per milliliter.

Dosage Forms. The pharmaceutical compositions of this invention can be administered by any means that effects contact of the active ingredients with the site of action in the body of a warm-blooded animal. For example, the means can be oral, transdermal, by inhalation, or parenteral (i.e., subcutaneous, intravenous, intramuscular or intraperitoneal). Alternatively or concurrently, the means of administration can be by more than one route (e.g., oral and parenteral). A most preferred means of administration is by the oral route (i.e., ingestion).

The active ingredients can be administered by the oral route in solid dosage forms, such as tablets, capsules, and powders, or in liquid dosage forms, such as elixirs, syrups, and suspensions. The pharmaceutical compositions of this invention also can be administered parenterally, in sterile liquid dosage forms. The pharmaceutical composition is preferably made in the form of a dosage unit containing a particular amount of each active ingredient.

In general, the pharmaceutical compositions of this invention can be prepared by conventional techniques, as are described in *Remington's Pharmaceutical Sciences*, a standard reference in this field [Gennaro A R, Ed. Remington: The Science and Practice of Pharmacy. $20^{th}$ Edition. Baltimore: Lippincott, Williams & Williams, 2000]. For therapeutic purposes, the active components of this combination therapy invention are ordinarily combined with one or more adjuvants appropriate to the indicated route of administration. If administered per os, the components may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tabletted or encapsulated for convenient administration. Such capsules or tablets may contain a controlled-release formulation as may be provided in a dispersion of active compound in hydroxypropyl methylcellulose. Solid dosage forms can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Both the solid and liquid oral dosage forms can contain coloring and flavoring to increase patient acceptance.

Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The components may be dissolved in water, polyethylene glycol, propylene glycol, ethanol, corn oil, cottonseed oil, peanut oil, sesame oil, benzyl alcohol, sodium chloride, and/or various buffers. The indicated formulations can contain compatible auxiliaries and excipients, such as anti-oxidants, preservatives, stabilizing agents, emulsifiers, salts for influencing the osmotic pressure, and/or buffer substances.

Other adjuvants and modes of administration are well and widely known in the pharmaceutical art.

Pharmaceutical compositions for use in the treatment methods of the invention may be administered orally or by intravenous administration. Oral administration of the therapy is preferred. Dosing for oral administration may be with a regimen calling for single daily dose, or for a single dose every other day, or for multiple, spaced doses throughout the day.

Calcium and magnesium ions exhibit complementary biological activity. Therefore, a combination therapy comprising a first quantity of L-carnitine calcium valproate and a second quantity of L-carnitine magnesium valproate is expected to provide synergistic therapeutic benefits. A combination therapy having molar ratios of 1:10 to 10:1 L-carnitine calcium valproate to L-carnitine magnesium valproate provides known quantities of valproate, L-carnitine, calcium, and magnesium, each having therapeutic benefit. The active agents which make up the combination therapy may be administered simultaneously, either in a combined dosage form or in separate dosage forms intended for substantially simultaneous oral administration. The active agents which make up the therapy may also be administered sequentially, with either active component being administered by a regimen calling for two-step ingestion. Thus, a regimen may call for sequential administration of the active agents with spaced-apart ingestion of the separate, active agents. The time period between the multiple ingestion steps may range from a few minutes to several hours, depending upon the properties of each active agent such a potency, solubility, bioavailability, plasma half-life and kinetic profile of the agent, as well as depending upon the age and condition of the patient. The active agents of the therapy whether administered simultaneously, substantially simultaneously, or sequentially, may involve a regimen calling for administration of one active agent by oral route and the other active agent by intravenous route. Whether the active agents of the therapy are administered by oral or intravenous route, separately or together, each such active agent will be contained in a suitable pharmaceutical formulation of pharmaceutically-acceptable excipients, diluents or other formulations components.

Clinical Uses of L-Carnitine Valproate Salts

The present invention provides methods for the reproducible preparation of pharmaceutical quality L-carnitine valproate salts as well as methods for formulation into pharmaceutical dosage forms using conventional pharmaceutical techniques. In addition, the inventors have shown that aqueous solutions of an L-carnitine valproate salt are readily prepared. Aqueous solutions of an L-carnitine valproate salt comprise fully ionized solutions of L-carnitine, calcium or magnesium ions, and valproate ions which, after parenteral administration to a subject, are completely bioavailable. Given this solubility, an L-carnitine valproate salt, when administered per os to a subject, is expected to exhibit a valproate bioavailability at least about 90% relative to intravenous infusion of valproate, a bioavailability that is equivalent to or exceeds that of divalproex sodium. On these bases, therefore, the inventors expect that an L-carnitine valproate salt of the present invention may be administered to subjects in need of valproate therapy as a therapeutically effective and biologically available substitute for valproic acid, divalproex sodium, valproate sodium, and other valproate salt compositions.

On this basis, the inventors expect that an L-carnitine valproate salt of the present invention may be substituted for valproic acid, divalproex sodium, valproate sodium and other valproate salt compositions in compositions useful for the treatment of neurological disorders as disclosed, by way of example, in U.S. Patent Applications 20050095579, 20050090548, 20050090449, 20050075282, 20050070524, and 20050065340, as well as in U.S. Pat. Nos. 6,406,716, 6,323,236, 6,287,598, and 5,945,416 and in international patents EP 1371366 A1, EP 0966967 A3, EP 1158973 B1, WO 2005070461, WO 2005063297, WO 2005051915, WO 2005049040, and WO 2004101603. Further, an L-carnitine valproate salt of the present invention may be substituted for valproic acid, divalproex sodium, valproate sodium and other valproate salt compositions in compositions useful for the treatment of immunological disorders as disclosed, by way of example, in U.S. Patent Applications 20050119261, 20050090553, 20050065596, 20050065173, 20050054091, as well as in U.S. Pat. Nos. 5,506,224 and 5,432,176 and in international patents EP 1529527 A1, EP 1293205 A1, EP 1170008 A1, EP 1301184 B1, WO 2005023179, WO 2005018578, WO 2004113305, WO 2004096216, WO 2004096224, and WO 2004050076. Likewise, the inventors expect that an L-carnitine valproate salt of the present invention may be substituted for valproic acid, divalproex sodium, valproate sodium and other valproate salt compositions in compositions useful for the treatment of viral-related disorders as disclosed, by way of example, in the report of Smith [Retrovirology Sep. 19, 2005, 2(1): 56], Cohen [Science Aug. 12, 2005, 309(5737): 999-1000], Lehrman et al. [Lancet Aug. 13, 2005, 366(9485): 549-555], and Ylisastigui et al. [AIDS May 21, 2004, 18(8): 1101-1108].

Since young age and polytherapy including valproate are primary risk factors for valproate-induced L-carnitine deficiency and valproate-related hepatic failure (Bohan et al., vide infra), the inventors expect that L-carnitine valproate salts of the present invention afford distinct advantages over conventional valproate compositions. These advantages are particularly significant for patients who are at risk for L-carnitine deficiency. Specifically, neonates and children cannot endogenously synthesize sufficient L-carnitine to meet physiological needs. Administration of valproate to neonates and children, therefore, exacerbates a pre-existing L-carnitine deficiency. In contrast, administration of an L-carnitine valproate salt of the present invention advantageously provides both the medication valproate and exogenous L-carnitine and addresses both the therapeutic and the physiological needs of subjects such as neonates and children, who lack the ability to meet endogenous requirements for L-carnitine.

Based on the molecular composition, each gram of L-carnitine calcium valproate provides about 0.58 g of valproate and about 0.33 g of L-carnitine. Likewise, each gram of L-carnitine magnesium provides about 0.60 g of valproate and about 0.34 g of L-carnitine. Exposure of an L-carnitine valproate salt of the present invention to the acidity of the stomach will cause dissociation of the salt into some or all of its component substituents. Once dissociated, valproate is known to be fully bioavailable. The bioavailability of L-carnitine is more variable. Conventional L-carnitine exhibits a bioavailability of 15-20% of the administered dose, and if the L-carnitine valproate salt of the present invention is completely dissociated in the stomach, the L-carnitine component of the salt will exhibit a bioavailability of 15-20% of the administered dose. However, divalent cations such as calcium and magnesium are known to alter the uptake of dietary constituents from the gastrointestinal tract. Therefore, if the L-carnitine component of the salt remains bound to the calcium or magnesium component of the salt, its uptake may be greater than 15-20%.

The following examples present representative compositions of the present invention. The examples are representative of the scope of the invention, and as such are not to be considered or construed as limiting the invention recited in the appended claims.

EXAMPLE 1

Figure 2:
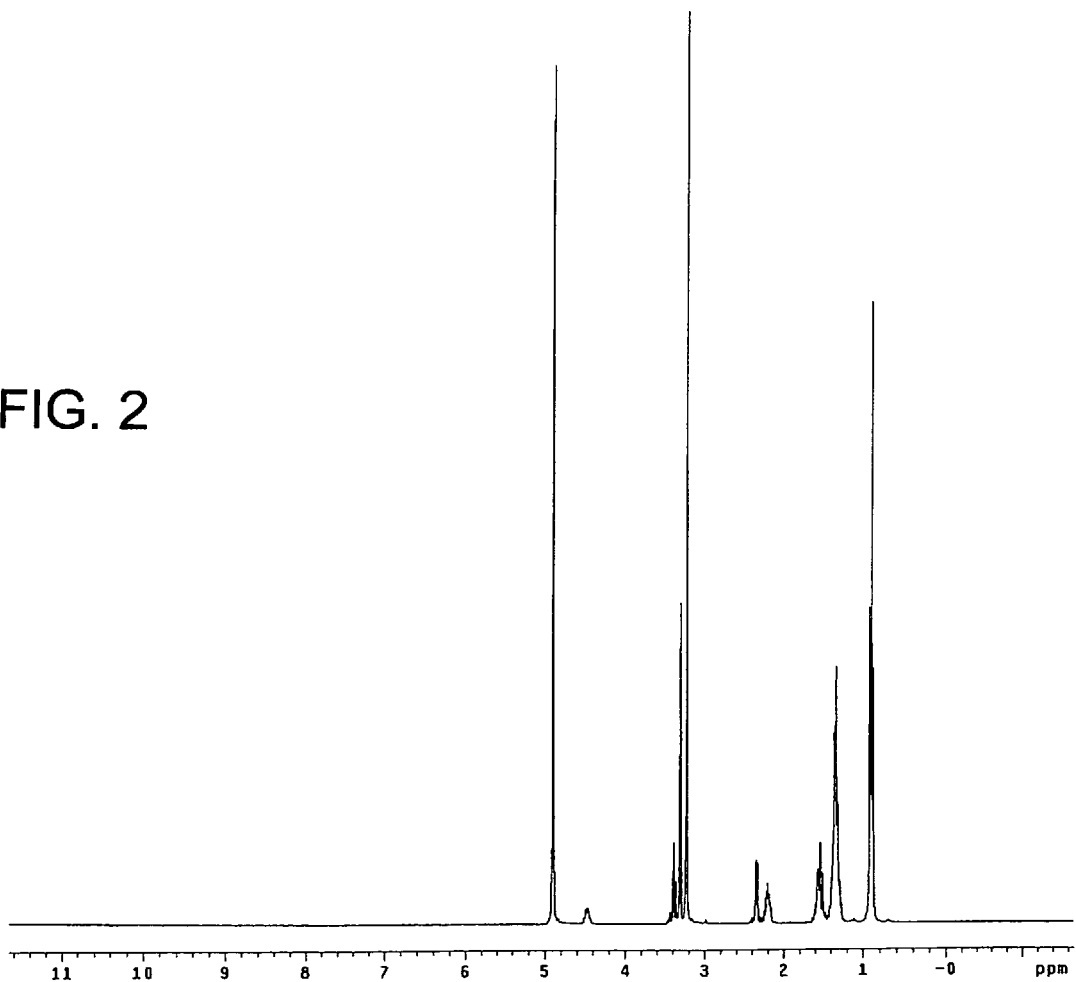
FIG. 2 is the $^1$H-NMR spectrum of L-carnitine calcium valproate in perdeutero-methanol solution.

Preparation of L-Carnitine Calcium Valproate. A Solution of L-Carnitine (0.5 g; 0.003 mol) was dissolved in 10 mL of water and a solution of valproic acid (0.82 g; 0.006 mol) in 5 mL of methanol was added in one portion. A clear solution resulted. Calcium hydroxide (0.22 g; 0.003 mol) was added in portions, and the resulting slurry was stirred at room temperature overnight. The slightly cloudy solution was clarified by filtration, and the filtrate was concentrated under vacuum at a temperature of less than about 70° C. to provide 1.22 g of product, L-carnitine calcium valproate, a white solid. The structure and composition of the product were confirmed by $^1$H-NMR analysis (FIG. 2). When the NMR spectrum of L-carnitine calcium valproate was compared to the NMR spectrum of valproic acid (FIG. 1), it was evident that the molar ratio of L-carnitine to valproate was approximately 1:2, as expected. (Calcium is not observed by NMR.) Further, the chemical shifts reflected the formation of an L-carnitine valproate salt. L-Carnitine calcium valproate had a melting point of 171.2° C. (with decomposition and release of trimethylamine). L-Carnitine calcium valproate readily dissolved in water or aqueous solutions. L-Carnitine calcium valproate had no odor and no objectionable taste.

EXAMPLE 2

Figure 3:
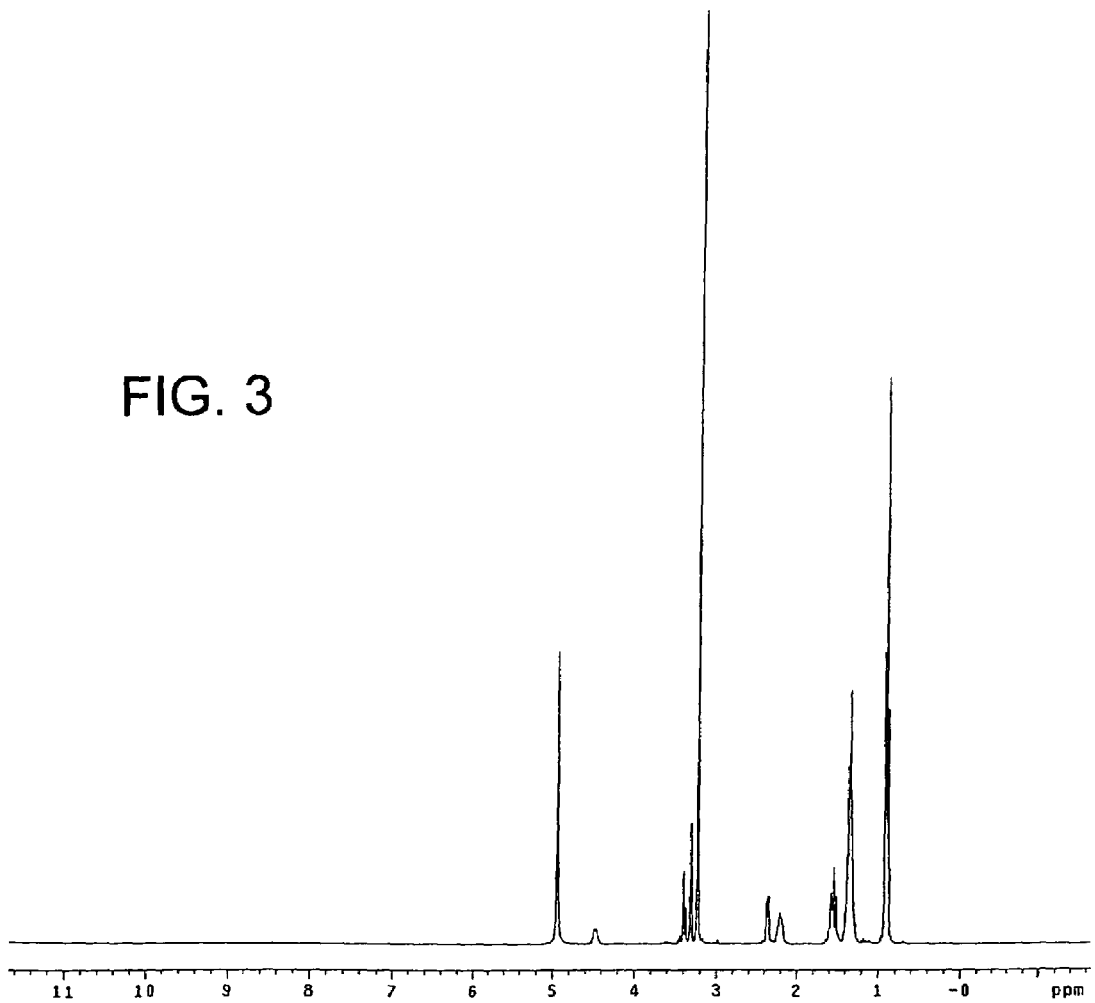
FIG. 3 is the $^1$H-NMR spectrum of L-carnitine magnesium valproate in perdeutero-methanol solution.

Preparation of L-Carnitine Magnesium Valproate. A Slurry of L-carnitine (0.5 g; 0.003 mol) in 10 mL of ethanol was prepared and valproic acid (0.82 g; 0.006 mol) was added in one portion. Magnesium ethoxide (0.35 g; 0.003 mol) was added in portions, and the resulting slurry was stirred at room temperature for an hour. The resulting clear solution was stirred an additional 3 hours. The solution was concentrated under vacuum at a temperature of less than about 70° C. to provide 1.20 g of product, L-carnitine magnesium valproate, a white solid. The structure and composition of the product were confirmed by $^1$H-NMR analysis (FIG. 3). When the NMR spectrum of L-carnitine magnesium valproate was compared to the NMR spectrum of valproic acid (FIG. 1), it was evident that the molar ratio of L-carnitine to valproate was approximately 1:2, as expected. (Magnesium is not observed by NMR.) Further, the chemical shifts reflected the formation of an L-carnitine valproate salt. L-Carnitine magnesium valproate had a melting point of 77.2° C. L-Carnitine magnesium valproate readily dissolved in water or aqueous solutions. L-Carnitine magnesium valproate had a slight amine odor and no objectionable taste.

EXAMPLE 3

Preparation of L-Carnitine Calcium Valproate Hydrate and L-Carnitine magnesium valproate hydrate. The effects of storage of the L-carnitine valproate salts of Examples 1 and 2 in ambient atmospheres were monitored for 6 days. For comparison, L-carnitine (Sigma Aldrich Chemical Co.), sodium valproate (Sigma Aldrich Chemical Co.), and divalproex sodium were also monitored in the same manner. The experiment was performed by weighing portions of each compound into a tared glass container and periodically monitoring the gross weight of the compound+container over a 6 day period. Results are summarized in the table below.

TABLE

Data

| Material | Net weight, initial | Net weight, final | Conclusion & Observations |
|---|---|---|---|
| L-Carnitine (Sigma Aldrich) | 208 mg | >227 mg | The sample absorbed water from the atmosphere and the weight increased. The material adhered to the glass vessel and gradually dissolved in the absorbed water. Material is hygroscopic. |
| Sodium valproate (Sigma Aldrich) | Not available | Not available | Within seconds, the sample began to absorb water from the atmosphere and the weight increased. A reliable initial weight could not be determined. Material is very hygroscopic. |
| Divalproex sodium | 100 mg | 100 mg | Mass of the material did not change. Material is not hygroscopic. |
| L-Carnitine calcium valproate | 194 mg | 202 mg (+5%) | Appearance and mobility of the material did not change. Material absorbed water and was converted to a hydrate, which is further described below. |
| L-Carnitine magnesium valproate | 142 mg | 163 mg (+15%) | Material absorbed water and was converted to a hydrate, which is further described below. |

L-Carnitine calcium valproate hydrate is formed by exposure of L-carnitine calcium valproate to water vapor. L-Carnitine calcium valproate hydrate is a freely mobile white solid having a melting point of about 112° C. (with decomposition and release of trimethylamine).

L-Carnitine magnesium valproate hydrate is formed by exposure of L-carnitine magnesium valproate to water vapor. L-Carnitine magnesium valproate hydrate is a nearly colorless crystalline solid having a crystal structure of nearly transparent spars having a melting point of about 43° C. (with decomposition and release of trimethylamine).

Neither L-carnitine alkaline earth metal valproate hydrate had an objectionable taste.

EXAMPLE 4

Attempted preparation of L-carnitine alkaline earth metal valproates using molar ratios different from 1:1:2. Preparation of L-carnitine alkaline earth metal valproates was attempted using non-stoichiometric molar ratios, in other words, molar ratios of L-carnitine to calcium or magnesium to valproate different from 1:1:2. If the molar ratio of L-carnitine to calcium or magnesium to valproate is 1:1:1, a solid product does not form, and a gummy oil is obtained. If the molar ratio of L-carnitine to calcium or magnesium to valproate is 1:1:0.5, a solid product does not form, and a gummy oil is obtained.

The following examples present hypothetically useful therapeutic uses of representative pharmaceutical compositions of the present invention and their anticipated outcomes in treating neurological diseases in subjects requiring such treatment. The examples are representative of the scope of the invention, and as such are not to be considered or construed as limiting the invention recited in the appended claims.

EXAMPLE 5

L-Carnitine calcium valproate of the present invention in the treatment of epilepsy. The therapeutic benefit of L-carnitine calcium valproate of the present invention is compared with that of sodium valproate in an open, comparative clinical trial in epileptic patients. Patients in the study population exhibit symptoms such as tonic-clonic convulsions, tonic nonfocal convulsions, simple absence seizures, absence attacks associated with generalized convulsions, partial convulsions, West syndrome or Lennox-Gastaut syndrome. The study population has previously been treated with sodium valproate (alone or in combination with other drugs) for a minimum of 6 months. Then treatment is substituted with an L-carnitine calcium valproate of the present invention (alone or combined with other drugs) for 3 months. At the beginning of the study, and at regular intervals thereafter, each subject receives a physical examination, including blood draws for clinical analysis of L-carnitine and total carnitine. In addition, each subject responds to questions about their health and well-being, including questions about episodes of malaise, fatigue, or nausea which they may have experienced during the course of the study. The following results are expected to be observed following administration of an L-carnitine calcium valproate salt of the present invention for 3 months. The percentage of patients without convulsions is expected to increase significantly. The number of patients with no convulsions or only occasional convulsions is expected to increase significantly. Patients with generalized nonconvulsive or partial epilepsy are expected to obtain significantly greater therapeutic benefit from treatment with the L-carnitine calcium valproate salt rather than sodium valproate, although patients in all other types of epilepsy are expected to obtain equivalent therapeutic benefit from the L-carnitine calcium valproate salt or sodium valproate treatment. Patients who receive the L-carnitine calcium valproate salt are expected to experience fewer side effects (e.g., gastric discomfort or ulceration, malaise, fatigue or nausea). A comparison of the serum concentrations of L-carnitine and total carnitine at the initial time point, at study intervals following administration of sodium valproate, and at study intervals following administration of L-carnitine calcium valproate of the invention is expected to show a decline from initial serum concentrations of L-carnitine and total carnitine during receipt of sodium valproate. However, during receipt of L-carnitine calcium valproate, the serum concentrations of L-carnitine and total carnitine are expected to increase toward initial concentrations. It is expected that this normalization in serum concentrations of L-carnitine and total carnitine will mitigate against valproate-related L-carnitine deficiency and hepatoxicity.

EXAMPLE 6

L-Carnitine magnesium valproate of the present invention in the treatment of epilepsy. The therapeutic benefit of an L-carnitine magnesium valproate salt of the present invention is compared with that of sodium valproate in an open, comparative clinical trial in epileptic patients. Patients in the study population exhibit symptoms such as tonic-clonic convulsions, tonic nonfocal convulsions, simple absence seizures, absence attacks associated with generalized convulsions, partial convulsions, West syndrome or Lennox-Gastaut syndrome. The study population has previously been treated with sodium valproate (alone or in combination with other drugs) for a minimum of 6 months. Then treatment is substituted with L-carnitine magnesium valproate (alone or combined with other drugs) for 3 months. At the beginning of the study, and at regular intervals thereafter, each subject receives a physical examination, including blood draws for clinical analysis of L-carnitine and total carnitine. In addition, each subject responds to questions about their health and well-being, including questions about episodes of malaise, fatigue, or nausea which they may have experienced during the course of the study. The following results are expected to be observed following administration of L-carnitine magnesium valproate for 3 months. The percentage of patients without convulsions is expected to increase significantly. The number of patients with no convulsions or only occasional convulsions is expected to increase significantly. Patients with generalized nonconvulsive or partial epilepsy are expected to obtain significantly greater therapeutic benefit from treatment with L-carnitine magnesium valproate rather than sodium valproate, although patients in all other types of epilepsy are expected to obtain equivalent therapeutic benefit from L-carnitine magnesium valproate or sodium valproate treatment. Patients who receive the L-carnitine magnesium valproate salt are expected to experience fewer side effects (e.g., gastric discomfort or ulceration, malaise, fatigue or nausea). A comparison of the serum concentrations of L-carnitine and total carnitine at the initial time point, at study intervals following administration of sodium valproate, and at study intervals following administration of L-carnitine magnesium valproate of the invention is expected to show a decline from initial serum concentrations of L-carnitine and total carnitine during receipt of sodium valproate. However, during receipt of L-carnitine magnesium valproate, the serum concentrations of L-carnitine and total carnitine are expected to increase toward initial concentrations. It is expected that this normalization in serum concentrations of L-carnitine and total carnitine will mitigate against valproate-related L-carnitine deficiency and hepatoxicity.

All mentioned references are incorporated by reference as if here written. When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

Without further elaboration, it is expected that one skilled in the art can, using the preceding description, utilize the present invention to its fullest extent. The specific embodiments are, therefore, to be construed as merely illustrative, and not limitative of the remainder of the disclosure in any way whatsoever.

We claim:

1. An L-carnitine valproate composition, having the molecular formula $C_{23}H_{45}NO_7M^{2+}$ and the molecular structure:

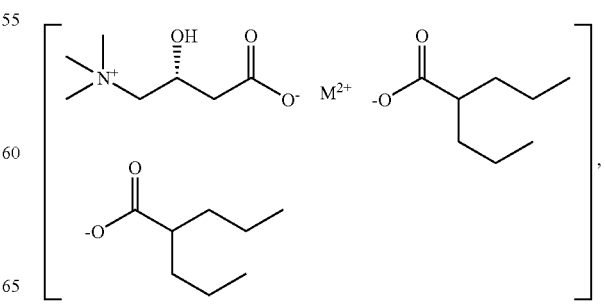

wherein $M^{2+}$ is calcium or magnesium.

2. The L-carnitine valproate composition of claim 1, wherein the composition comprises L-carnitine, calcium or magnesium, and valproate in a stoichiometric ratio of 1:1:2.

3. A method for preparing an L-carnitine valproate composition of claim 1, comprising combining a calcium or magnesium compound, an aqueous solution of L-carnitine, and an alcohol solution of valproic acid in a stoichiometric ratio of 1:1:2, reacting to provide an aqueous alcohol solution of the L-carnitine valproate composition, and isolating the L-carnitine valproate composition from the aqueous alcohol solution.

4. The method of claim 3, wherein the calcium compound is selected from the group consisting of calcium hydroxide, calcium oxide, calcium carbonate, and calcium chloride.

5. The method of claim 3, wherein the magnesium compound is selected from the group consisting of magnesium hydroxide, magnesium oxide, magnesium carbonate, and magnesium chloride.

6. A pharmaceutical formulation for the concomitant administration of L-carnitine and valproate, comprising an L-carnitine alkaline earth metal valproate having the molecular formula $C_{23}H_{45}NO_7M^{2+}$ and the molecular structure:

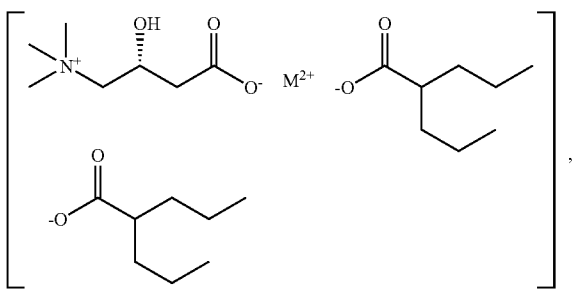

wherein $M^{2+}$ is calcium or magnesium.

7. A method of formulating an L-carnitine valproate salt of an alkaline earth metal, comprising preparing a dosage form comprising an L-carnitine valproate salt of an alkaline earth metal having the molecular formula $C_{23}H_{45}NO_7M^{2+}$ and the molecular structure:

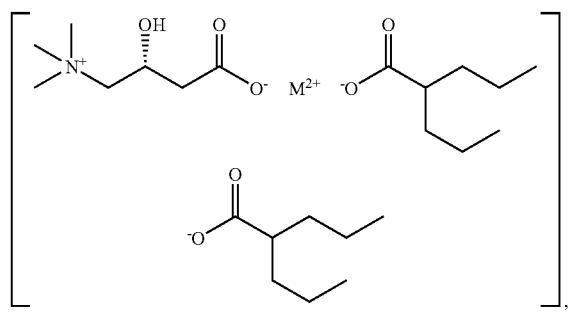

wherein $M^{2+}$ is calcium or magnesium in an amount that is sufficient to provide a therapeutically effective first amount of valproate and a therapeutically effective second amount of L-carnitine to a warm-blooded animal.

8. The method of claim 7 wherein the dosage form is a solid dosage form or a liquid dosage form.

9. The method of claim 8 wherein the liquid dosage form comprises an aqueous solution of L-carnitine calcium valproate having a concentration of valproate in the range from about 1 mg/mL to about 150 mg/mL.

10. The method of claim 9, further comprising sterilizing the formulation.

11. A pharmaceutical formulation comprising a therapeutically effective first quantity of L-carnitine calcium valproate and a therapeutically effective second quantity of L-carnitine magnesium valproate.

* * * * *